United States Patent
Chen

(10) Patent No.: US 9,107,944 B2
(45) Date of Patent: *Aug. 18, 2015

(54) IMMUNOLOGICALLY MODIFIED CARBON NANOTUBES FOR CANCER TREATMENT

(71) Applicant: THE UNIVERSITY OF CENTRAL OKLAHOMA, Edmond, OK (US)

(72) Inventor: Wei R. Chen, Edmond, OK (US)

(73) Assignee: The University of Central Oklahoma, Edmond, OK (US)

( * ) Notice: Subject to any disclaimer, the term of this patent is extended or adjusted under 35 U.S.C. 154(b) by 24 days.

This patent is subject to a terminal disclaimer.

(21) Appl. No.: 13/755,105

(22) Filed: Jan. 31, 2013

(65) Prior Publication Data

US 2013/0172848 A1    Jul. 4, 2013

Related U.S. Application Data

(62) Division of application No. 13/037,171, filed on Feb. 28, 2011, now Pat. No. 8,664,198.

(51) Int. Cl.

| A61K 41/00 | (2006.01) |
|---|---|
| A61N 5/06 | (2006.01) |
| A61K 39/00 | (2006.01) |
| B82Y 5/00 | (2011.01) |
| C12N 5/00 | (2006.01) |

(52) U.S. Cl.
CPC ......... *A61K 41/0057* (2013.01); *A61K 39/0011* (2013.01); *A61K 41/0052* (2013.01); *A61N 5/062* (2013.01); *B82Y 5/00* (2013.01); *C12N 5/0068* (2013.01); *A61K 2039/55583* (2013.01); *A61K 2039/6087* (2013.01); *C12N 2533/30* (2013.01); *Y10S 977/746* (2013.01); *Y10S 977/918* (2013.01)

(58) Field of Classification Search
CPC ....... A61K 41/0057; B82Y 5/00; A61N 5/062
See application file for complete search history.

(56) References Cited

U.S. PATENT DOCUMENTS

| 5,747,475 A | 5/1998 | Nordquist et al. |
|---|---|---|
| 6,099,554 A | 8/2000 | Nordquist et al. |
| 6,149,671 A | 11/2000 | Nordquist et al. |
| 6,290,712 B1 | 9/2001 | Nordquist et al. |
| 6,316,007 B1 | 11/2001 | Nordquist et al. |
| 6,333,016 B1 | 12/2001 | Resasco et al. |
| 6,413,487 B1 | 7/2002 | Resasco et al. |
| 6,756,363 B1 | 6/2004 | Nordquist et al. |
| 6,919,064 B2 | 7/2005 | Resasco et al. |
| 6,955,800 B2 | 10/2005 | Resasco et al. |
| 6,962,892 B2 | 11/2005 | Resasco et al. |
| 6,994,907 B2 | 2/2006 | Resasco et al. |
| 7,094,386 B2 | 8/2006 | Resasco et al. |
| 7,153,903 B1 | 12/2006 | Barraza et al. |
| 7,459,138 B2 | 12/2008 | Resasco et al. |
| 7,585,482 B2 | 9/2009 | Resasco et al. |
| 7,737,259 B2 | 6/2010 | Chen et al. |
| 7,767,219 B2 | 8/2010 | Weber et al. |
| 2006/0222595 A1 | 10/2006 | Mukherjee et al. |
| 2009/0062785 A1 | 3/2009 | Harrison, Jr. et al. |
| 2010/0184669 A1 | 7/2010 | Harrison, Jr. et al. |
| 2010/0189650 A1 | 7/2010 | Kim et al. |

FOREIGN PATENT DOCUMENTS

WO    WO2008136773    11/2008

OTHER PUBLICATIONS

Alvarez W.E. et al., "Characterization of Single-Walled Carbon Nanotubes (SWNTs) Produced by CO Disproportionation on Co-Mo Catalysts", "Chem. Mater.", Mar. 19, 2002, pp. 1853-1858, vol. 14, Publisher: American Chemical Society.

Bachilo, S.M. et al., "Narrow (n,m)-Distribution of Single-Walled Carbon Nanotubes Grown Using a Solid Supported Catalyst", "Journal of American Chemical Society", Aug. 21, 2003, pp. 11186-11187, vol. 125, Publisher: American Chemical Society.

Castano, A.P. et al., "Photodynamic therapy and anti-tumor immunity", "Nature Reviews/Cancer", Jul. 1, 2006, pp. 535-545, vol. 6, Publisher: Nature Publishing Group.

Chen, W.R. et al., "Laser Immunotherapy: A novel treatment modality for metastatic tumors (Abstract Only)", "Molecular Biotechnology", Sep. 1, 2003, pp. 37-43, vol. 25, No. 1.

Chen, T. et al., "Heat Shock Protein 70, Released from Heat-Stressed Tumor Cells, Initiates Antitumor Immunity by Inducing Tumor Cell Chemokine Production and Activating Dendritic Cells via TLR4 Pathway", "The Journal of Immunology", 2009, pp. 1449-1459, vol. 182, Publisher: The American Association of Immunologists.

De Jong, S. et al., "Encapsulation in liposomal nanoparticles enhances the immunostimulatory, adjuvant and anti-tumor activity of subcutaneously administered CpG ODN", "Cancer Immunol Immunother", Jan. 23, 2007, pp. 1251-1264, vol. 56, Publisher: Springer-Verlag.

(Continued)

*Primary Examiner* — James D Anderson
(74) *Attorney, Agent, or Firm* — Fellers, Snider, Blankenship, Bailey & Tippens, P.C.

(57) ABSTRACT

A method for constructing a compound of immunologically modified nanotubes and method for using the compound to deliver immunoadjuvants to tumor cells and to produce targeted, synergistic photophysical and immunological reactions for cancer treatment. To prepare the immunologically modified nanotubes, carbon nanotubes are dissolved in a solution of glycated chitosan, an immunostimulant, hence using glycated chitosan as a surfactant for rendering the aqueous solution of nanotubes stable. The compound can be used for treatment of cancer. The method includes steps of intratumorally administering immunologically modified nanotubes and administering laser irradiation of the target tumor. The nanotube serves as a carrier to deliver immunoadjuvants to the tumor cells and serves as a light-absorbing agent in a cell body of a tumor in a host. Upon laser irradiation of target tumor cells, immunologically modified nanotubes inside the tumor cells can produce spatially and temporally synchronized photothermal and immunological reactions for cancer treatment.

6 Claims, 13 Drawing Sheets

(56) References Cited

OTHER PUBLICATIONS

Dewey, W.C. et al., "Cellular Responses to Combinations of Hypothermia and Radiation", "Radiology", May 1, 1977, pp. 463-474, vol. 123.

Dinauer, N. et al., "Selective targeting of antibody-conjugated nanoparticles to leukemic cells and primary T-lymphocytes", "Biomaterials", Oct. 1, 2005, pp. 5898-5906, vol. 26, No. 29, Publisher: Science Direct.

El-Sayed, I.H. et al., "Selective laser photo-thermal therapy of epithelial carcinoma using anti-EGFR antibody conjugated gold nanoparticles", "Cancer Letters", Jul. 28, 2006, pp. 129-135, vol. 239, No. 1, Publisher: Science Direct.

Fifis, T. et al., "Size-Dependent Immunogenicity: Therapeutic and Protective Properties of Nano-Vaccines against Tumors", "The Journal of Immunology", 2004, pp. 3148-3154, vol. 173, Publisher: The American Association of Immunologists, Inc.

Gannon, C.J., et al., "Carbon Nanotube-enhanced Thermal Destruction of Cancer Cells in a Noninvasive Radiofrequency Field", "Wiley InterScience", Oct. 24, 2007, pp. 2654-2665, Publisher: American Cancer Society.

Herrera, J.E. et al., "Raman Characterization of Single-Walled Nanotubes of Various Diameters Obtained by Catalytic Disproportionation of CO", "Journal of Nanoscience and Nanotechnology", 2003, pp. 1-6, vol. 3, No. 1, Publisher: American Scientific Publishers.

Hirsch, L.R. et al., "Nanoshell-mediated near-infrared thermal therapy of tumors under magnetic resonance guidance", "Proceedings of the National Academy of Sciences", Nov. 11, 2003, pp. 13549-13554, vol. 100, No. 23, Publisher: The National Academy of Sciences of the USA.

Huang, X. et al., "Determination of the Minimum Temperature Required for Selective Photothermal Destruction of Cancer Cells with the Use of Immunotargeted Gold Nanoparticles", "Phytochemistry and Photobiology", Jan. 18, 2006, pp. 412-417, vol. 82, No. 2, Publisher: American Society for Photobiology.

Ito, A. et al., "Cancer immunotherapy based on intrecellular hyperthermia using magnetite nanoparticles: a novel concept of 'heat-controlled necrosis'", "Cancer Immunol. Immunother.", Aug. 25, 2005, pp. 320-328, vol. 55, Publisher: Springer-Verlag.

Ito, A. et al., "Magnetite nanoparticle-loaded anti-HER2 immunoliposomes for combination of antibody therapy with hyperthermia", "Cancer Letters", Aug. 20, 2004, pp. 167-175, vol. 212, No. 2, Publisher: Science Direct.

Kam, N.W.S et al.,, "Carbon nanotubes as multifunctional biological transporters and near-infrared agents for selective cancer cell destruction", "Proceedings of the National Academy of Sciences", Aug. 16, 2005, pp. 11600-11605, vol. 102, No. 33, Publisher: The National Academy of Sciences of the USA.

Kitiyanan, B. et al., "Controlled production of single-wall carbon nanotubes by catalytic decomposition of CO on bimetallic Co-Mo catalysts", "Chemical Physics Letters", Feb. 4, 2000, pp. 497-503, vol. 317, Publisher: Elsevier Science, B.V.

Konig, K., "Multiphoton microscopy in life sciences (Abstract Only)", "Journal of Microscopy", Nov. 1, 2000, pp. 83-104, vol. 200, No. 2, Publisher: Oxford.

Li, L. et al., "A Novel Antiangiogenesis Therapy Using an Integrin Antagonist or Anti-FLK-1 Antibody Coated 90Y-Labeled Nanoparticles", "Int. J. Radiation Oncology Biol. Phys.", 2004, pp. 1215-1227, vol. 58, No. 4, Publisher: Elsevier.

Lovell, R. et al., "Effects of active and passive hyperthermia on heat shock protein 70 (HSP70)", "Amino Acids", Oct. 12, 2007, pp. 203-211, vol. 34, Publisher: Springer-Verlag.

McDevitt, M.R. et al., "Tumor Targeting with Antibody-Functionalized, Radiolabeled Carbon Nanotubes", "The Journal of Nuclear Medicine", Jul. 1, 2007, pp. 1180-1189, vol. 48, No. 7, Publisher: Society of Nuclear Medicine.

Pompeo, F. et al., "Water Solubilization of Single-Walled Carbon Nanotubes by Functionalization with Glucosamine", "Nano Letters", Jan. 26, 2002, pp. 369-373, vol. 2, No. 4, Publisher: American Chemical Society.

Resasco, D.E. et al., "Controlled growth of SWCNT on solid catalysts with narrow (n,m) distribution", "Electronic Properties of Synthetic Nanostructures", 2004, pp. 27-31, Publisher: American Institute of Physics.

Rylander, M.N. et al., "Heat Shock Protein Expression and Injury Optimization for Laser Therapy Design", "Lasers in Surgery and Medicine", 2007, pp. 731-746, vol. 39, Publisher: Wiley-Liss, Inc.

Sapareto, S.A. et al., "Thermal Dose Determination in Cancer Therapy", "Int. J. Radiation Oncology Biol. Phys.", 1984, pp. 787-800, vol. 10, Publisher: Pergamon Press Ltd.

Song, S. et al., "Glycated chitosan as a new non-toxic immunological stimulant", "Immunopharmacology and Immunotoxicology", 2009, pp. 202-208, vol. 31, No. 2, Publisher: Informa UK Ltd.

Tan, Y. et al., "Dispersion of Single-Walled Carbon Nanotubes of Narrow Diameter Distribution", "J. Phys. Chem.", Jul. 9, 2005, pp. 14454-14460, vol. 109, Publisher: American Chemical Society.

PCT ISA/US, "International Search Report and Written Opinion for PCT/US2012/027021", Jun. 8, 2012.

Yu, J. et al., "Synthesis of Near-Infrared-Absorbing Nanoparticle-Assembled Capsules", "Chem. Mater.", Feb. 21, 2007, pp. 1277-1284, vol. 19, Publisher: American Chemical Society.

Zaharoff, D.A. et al., "Chitosan solution enhances the immunoadjuvant properties of GM-CSF", "Vaccine", Nov. 5, 2007, pp. 8673-8686, vol. 25, No. 52, Publisher: Science Direct.

Zhang, H-G et al., "Hyperthermia on immune regulation: A temperature's story", "Cancer Letters", Nov. 28, 2008, pp. 191-204, vol. 271, No. 2, Publisher: Science Direct.

Zhou, F. et al., "New Insights of Transmembranal Mechanism and Subcellular Localization of Noncovalently Modified Single-Walled Carbon Nanotubes", "Nano Letters", Apr. 6, 2010, pp. 1677-1681, vol. 10, Publisher: American Chemical Society.

Zhou, F. et al., "Cancer photothermal therapy in the near-infrared region by using single-walled carbon nanotubes", "Journal of Biomedical Optics", Mar. 1, 2009, pp. 1-7, vol. 14, No. 2, Publisher: SPIE.

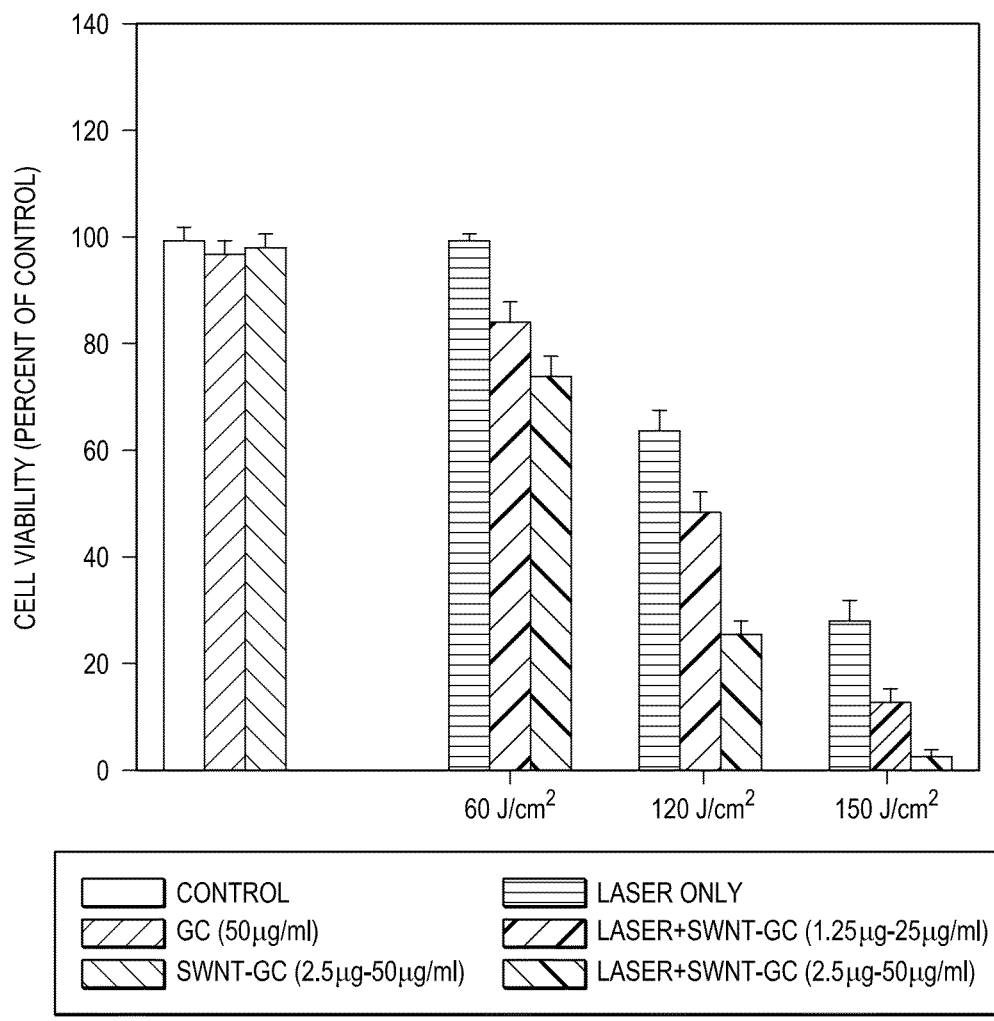

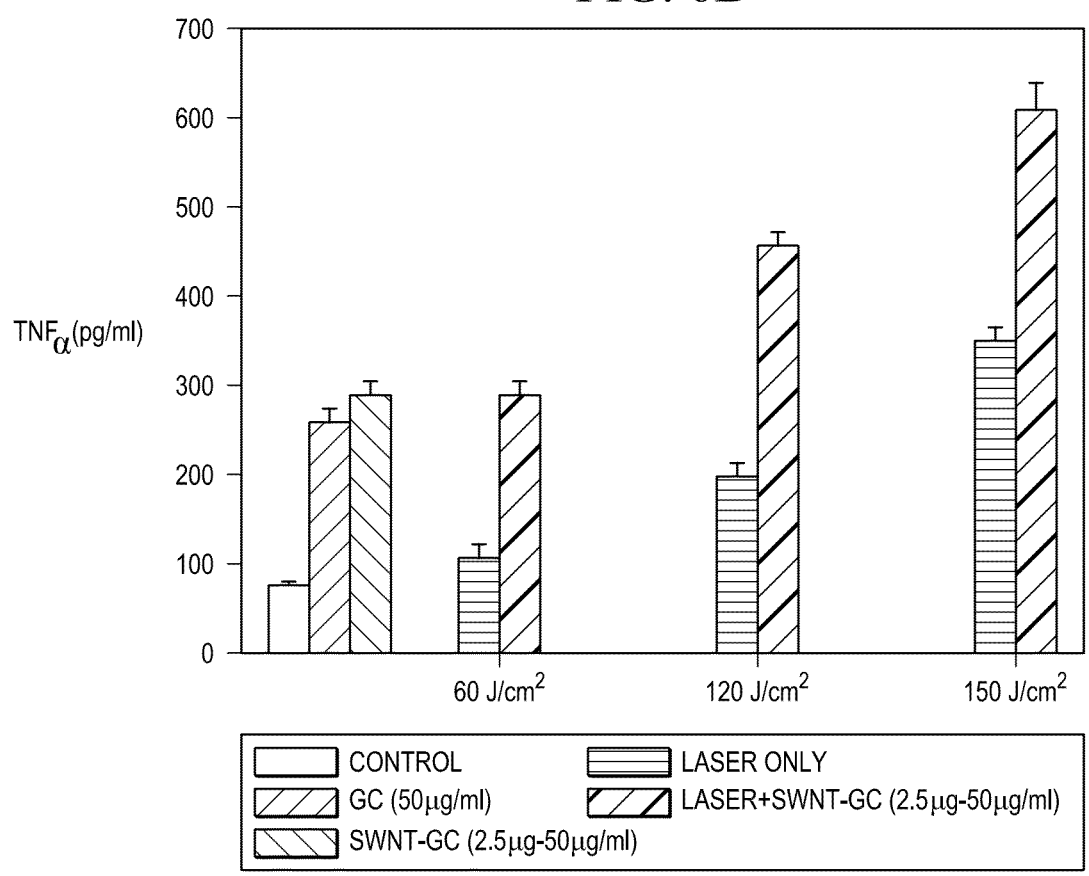

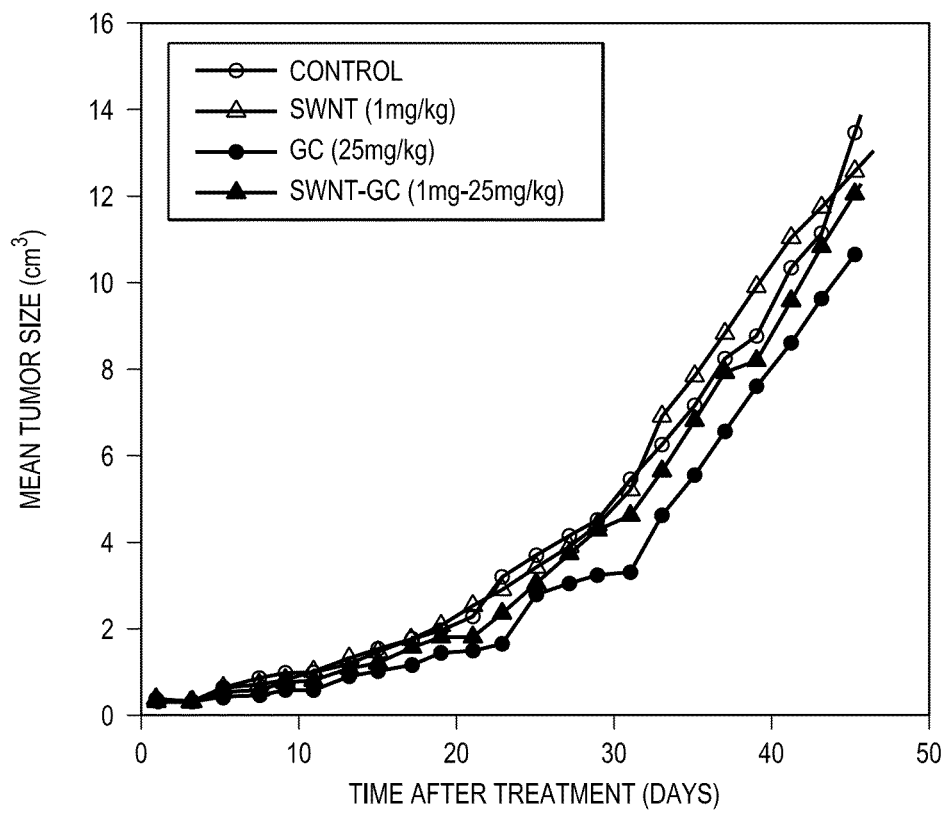
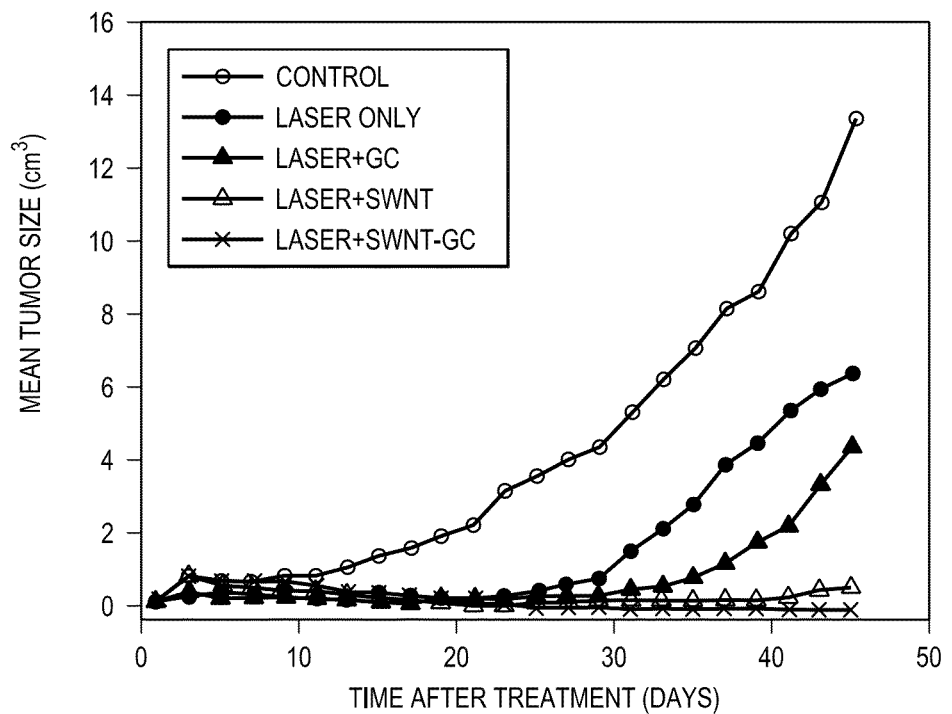
FIG. 7B

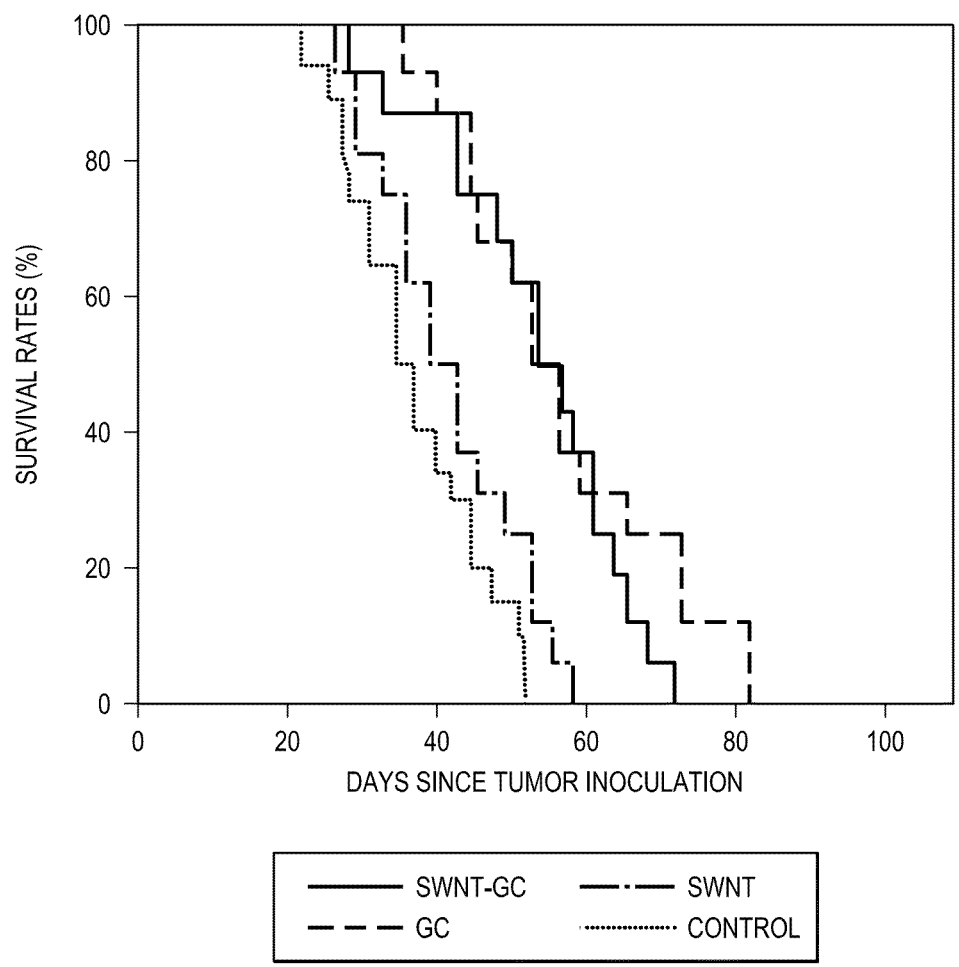

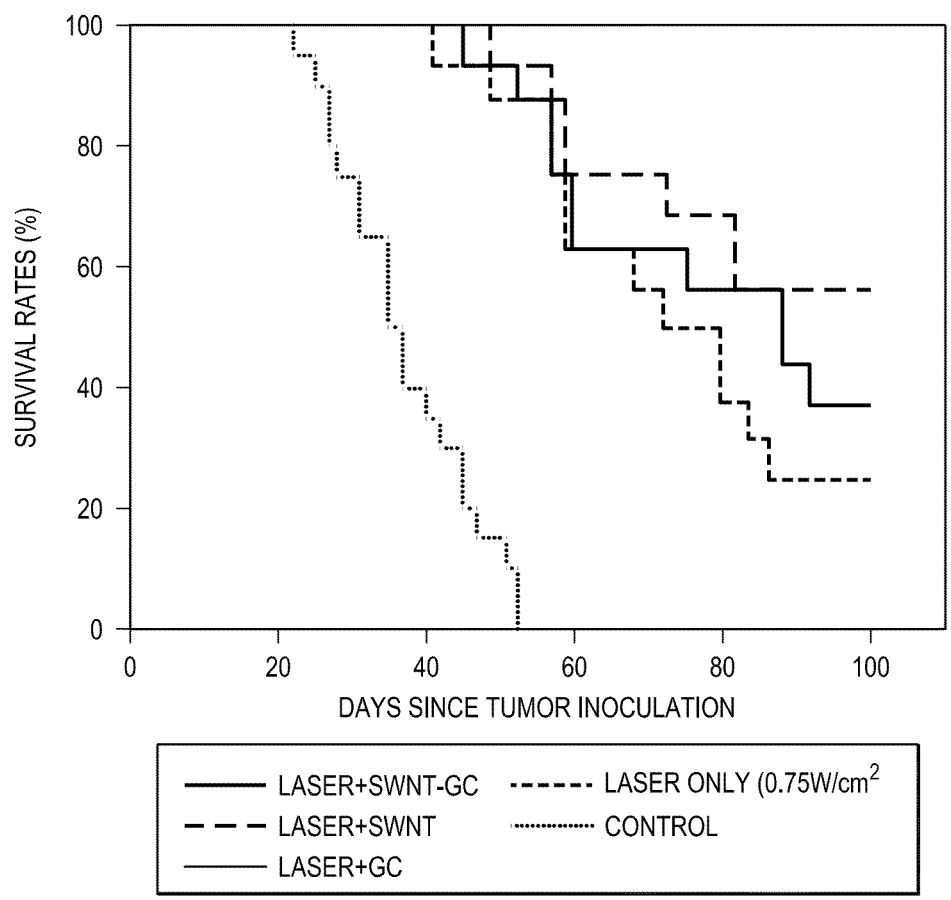

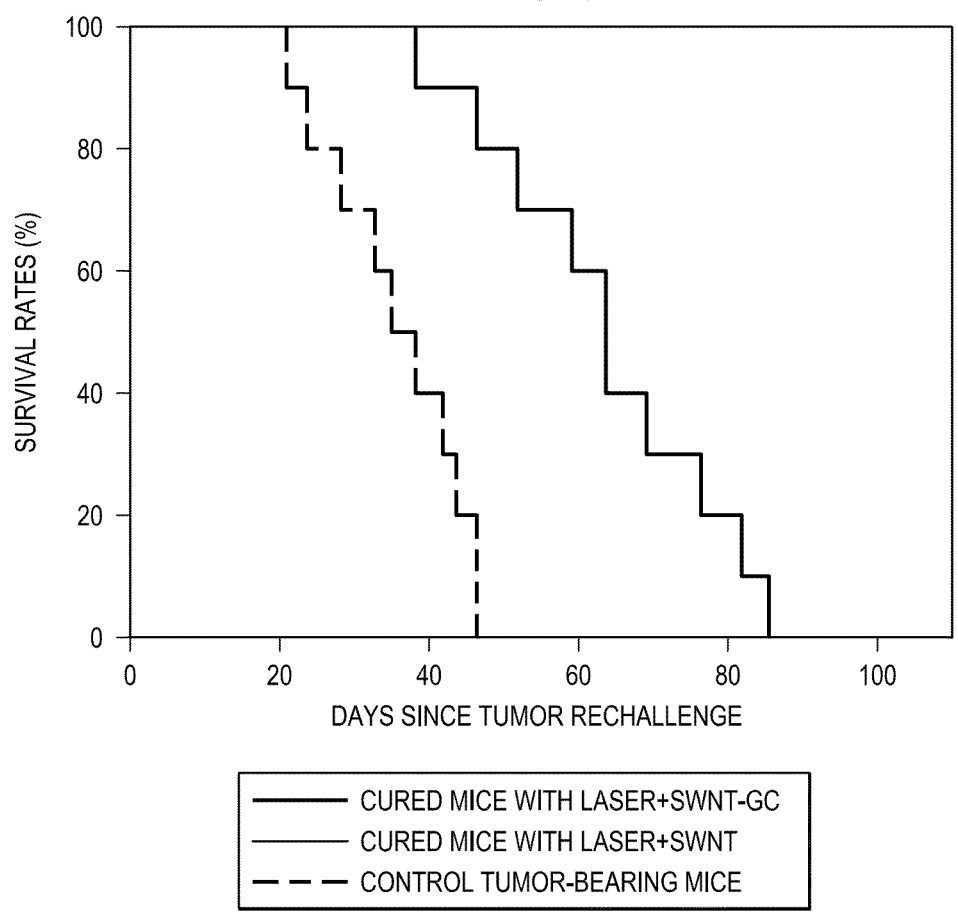

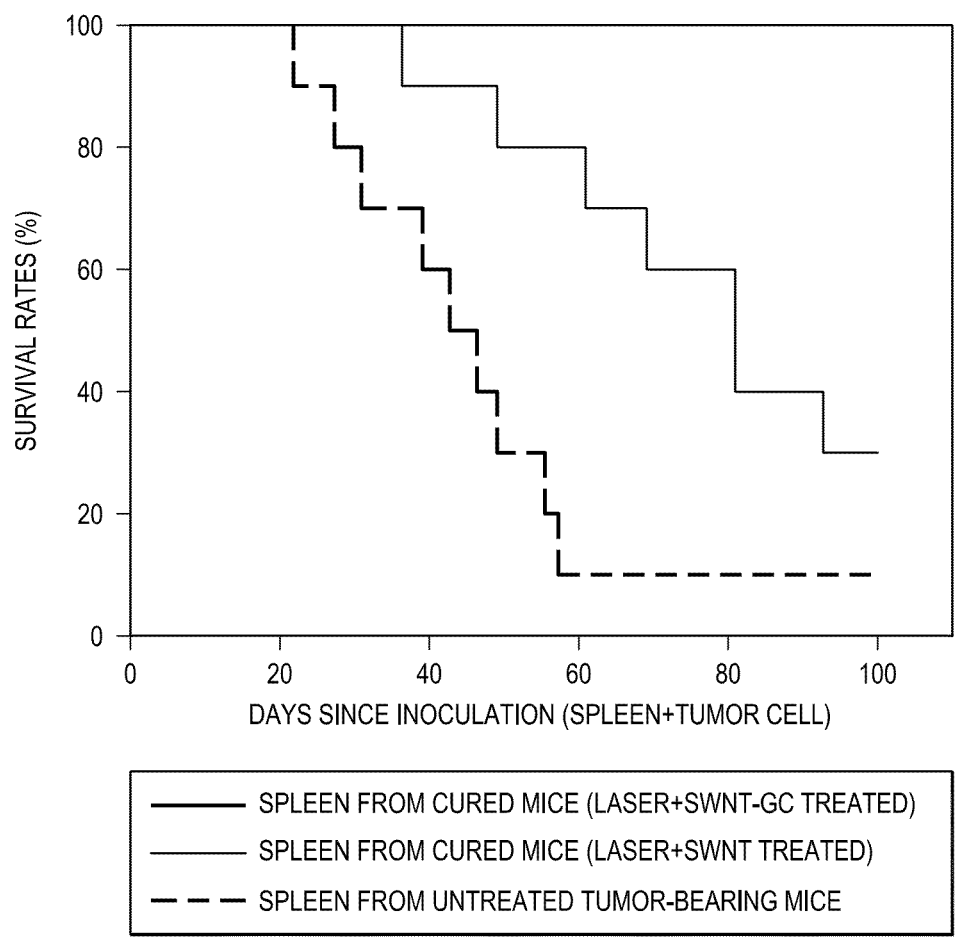

IMMUNOLOGICALLY MODIFIED CARBON NANOTUBES FOR CANCER TREATMENT

CROSS REFERENCE TO RELATED APPLICATIONS

This application is a Divisional of U.S. patent application Ser. No. 13/037,171 entitled "IMMUNOLOGICALLY MODIFIED CARBON NANOTUBES FOR CANCER TREATMENT," filed Feb. 28, 2011, the contents of which are hereby incorporated by reference.

FIELD OF THE INVENTION

This invention is related to the field of biomedical applications of nanotechnology. More particularly, the invention is related to a new compound of immunologically modified carbon nanotubes and the use of the compound for delivering immunoadjuvants to tumor cells and for producing targeted, synergistic photophysical and immunological reactions for cancer treatment.

BACKGROUND OF THE INVENTION

Nanotechnology has been used in the biomedical fields. Specifically, single-walled carbon nanotubes (SWNTs) have been applied in various biological systems. One intrinsic property of SWNTs is their ability to cross cellular membranes without eliciting cytotoxicity. Another intrinsic property of SWNTs is their strong optical absorbance in the near-infrared (NIR) region. It was reported that SWNTs could enhance thermal destruction of cells during NIR laser irradiation and radiofrequency irradiation. Since biological tissues are relatively transparent to light in the range of 700-1100 nm, the ideal SWNT for photothermal therapy should have an absorption band in the NIR region. Furthermore, it is desirable to have nanotubes with uniform size so that a narrow absorption peak can be used for effective optical irradiation. The CoMoCAT method, discussed in "Controlled production of single-wall carbon nanotubes by catalytic decomposition of CO on bimetallic Co—Mo catalysts" by Kitiyanan B, Alvarez W E, Harwell J H, Resasco D E (2000) in *Chem. Phys. Lett.* 317:497-503, incorporated herein by reference, produces SWNTs with a narrow and intense absorption band around 980 nm.

For biological applications, SWNTs should be prepared in aqueous suspension; surfactants are needed for stable dispersion to avoid aggregation of nanotubes. Sodium dodecylbenzene sulfonate (NaDDBS), sodium carboxymethylcellulose (NaCMC), and sodium cholate (NaCholate) are commonly used as surfactants for nanotubes.

The electronic structure of SWNTs is sensitive to changes in the surrounding electrostatic environment. For example, their optical response can be greatly changed by surface charge transfers or by adsorption of molecules. Therefore, it is crucial to have a SWNT solution with appropriate optical properties for biomedical applications.

Photothermal therapy can be effective for local cancer treatment due to the sensitivity of tumor cells to temperature elevation. Laser immunotherapy was developed to combine photothermal reaction with immunological stimulation to treat metastatic tumors. Its selective photothermal effect serves as the first line of assault on the tumor, using a combination of an NIR laser irradiation and a light-absorbing dye. An immunological stimulant is used concurrently to induce immunological responses. A new compound, glycated chitosan (GC), was developed as such an immunostimulant. Laser immunotherapy using GC and the light-absorbing dye has been proven to be highly effective in the treatment of metastatic tumors in pre-clinical studies. This method has also been used to treat late-stage breast cancer patients with promising outcomes.

SUMMARY OF THE INVENTION

Anti-tumor immunological response induced by local intervention is ideal for treatment of metastatic tumors. A novel immunologically modified nanotube system is constructed using glycated chitosan (GC), a potent immunoadjuvant, as an effective surfactant for single-walled carbon nanotubes (SWNTs). This novel SWNT-GC system has a long-term stability and it retains the absorption characteristics of SWNT and the immunological adjuvant function of GC. Locally administered SWNT-GC and irradiation of near-infrared light produced synergistic, simultaneous photothermal and immunological reactions in the treatment of tumor cells, both in vitro and in vivo. Laser+SWNT-GC resulted in highly effective tumor suppression in animal tumor models, with complete tumor regression and long-term survival in many cases. Tumor-bearing animals successfully treated with Laser+SWNT-GC established total resistance to subsequent tumor challenges. Passive adoptive immunity transfer using splenocytes as immune cells harvested from Laser+SWNT-GC-cured animals provided 100% immunity in naive recipients. Laser+SWNT-GC could prove to be a promising selective local treatment modality that induces systemic anti-tumor response, while minimizing adverse side effects.

To utilize the special absorption properties of the CoMoCAT SWNTs, and to immunologically enhance photothermal effects, a novel SWNT-GC system was designed in which GC simultaneously serves as an effective surfactant and a potent immunostimulant, providing two crucial functionalities to this novel system. SWNT-GC suspension is stable and it completely retains the light absorption characteristics of SWNTs and the immunological functions of GC. Using local laser+SWNT-GC treatment has resulted in significant tumor suppression and anti-tumor immunological responses in animal tumor models.

Furthermore, nanotubes can enter cells due to their size and electric properties. Nanotubes can serve as drug carriers. In the method of this invention, nanotubes carry the immunoadjuvant, GC, into the tumor cells. Therefore, under irradiation of a laser light of appropriate wavelength, SWNT-GC can produce temporally and spatially synchronized photothermal and immunological reactions in the target tumor cells. The SWNT-GC combination also has the potential to carry other therapeutic agents to tumors so that cancer can be treated with combination therapy of desired agents.

BRIEF DESCRIPTION OF THE DRAWINGS

FIG. 5. Viability of in vitro tumor cells under different treatments. Tumor cells were treated with GC (50 μg/ml), SWNT-GC (2.5 μg-50 μg/ml), laser only (60, 120, or 150 J/cm$^2$), or Laser+SWNT-GC (60, 120, or 150 J/cm$^2$; 1.25 μg-25 μg/ml or 2.5 μg-50 μg/ml). The treated cells were incubated in complete medium for 12 hours before assessing cell viability. Bars, means±SD (n=4).

FIG. 6B. In vitro immunological effects of SWNT-GC: TNFα secretion by macrophages stimulated by treated EMT6 cells. Macrophages were incubated for 24 hours with tumor cells (1:1) treated by GC (50 μg/ml), SWNT-GC (2.5 μg-50 μg/ml), laser light (60-150 J/cm$^2$), or Laser+SWNT-GC (60-150 J/cm$^2$, 2.5 μg-50 μg/ml). Cells without treatment incubated with macrophages were used as control. After incubation, supernatants were collected for the determination of TNFα. Bars, means±SD (n=4).

FIG. 7A. Effects on tumor burden of intratumoral injections (at day 0) of different components: (i) control, (ii) SWNT (1 mg/kg), (iii) GC (25 mg/kg), or (iv) SWNT-GC (1 mg-25 mg/kg); 12 mice/group. EMT6 cells were injected subcutaneously into the flanks of Balb/c female mice and treatment took place when tumors reached a size of approximately 300 nm$^3$.

FIG. 7B. Effects on tumor burden of intratumoral injections of different components, followed by laser irradiation (0.75 W/cm$^2$ for 10 minutes at day 0): (i) control, (ii) Laser, (iii) Laser+GC (25 mg/kg), (iv) Laser+SWNT (1 mg/kg), or (v) Laser+SWNT-GC (1 mg-25 mg/kg); 12 mice/group. EMT6 cells were injected subcutaneously into the flanks of Balb/c female mice and treatment took place when tumors reached a size of approximately 300 mm$^3$. Laser+SWNT-GC and Laser+SWNT were significantly more efficacious in tumor reduction as compared with other groups.

FIG. 8A. In vivo effects of SWNT and GC without laser irradiation: Animal Survival. Survival rates of tumor-bearing mice treated by intratumoral injections (at day 0) of different components: (i) SWNT-GC (1 mg-25 mg/kg), (ii) GC (25 mg/kg), (iii) SWNT (1 mg/kg), or (iv) control: 12 mice/group. EMT6 cells were injected subcutaneously into the flanks of Balb/c female mice and treatment took place when tumors reached a size of approximately 300 mm$^3$.

FIG. 8B. In vivo effects of SWNT and GC with laser irradiation: Animal Survival. Survival rates of tumor-bearing mice treated by intratumoral injections of different components, followed by laser irradiation (0.75 W/cm$^2$ for 10 minutes, day 0): (i) Laser+SWNT-GC (1 mg-25 mg·kg), (ii) Laser+SWNT (1 mg/·kg), (iii) Laser+GC (25 mg/kg), (iv) Laser, or (v) control; 12 mice/group. EMT6 cells were injected subcutaneously into the flanks of Balb/c female mice and treatment took place when tumors reached a size of approximately 300 mm$^3$. Laser+SWNT-GC and Laser+SWNT were significantly more efficacious in animal survival as compared with other groups.

FIG. 9. Tumor rechallenge of successfully treated mice. Tumor-bearing mice cured by Laser+SWNT-GC or Laser+SWNT treatment were challenged with 2×10$^6$ viable tumor cells 100 days after the initial inoculation. Naive mice of the same age were also inoculated with 2×10$^6$ viable tumor cells as controls. All the mice cured by Laser+SWNT-GC showed total resistance to the challenge; however, mice cured by laser+SWNT, while with a prolonged average survival time, were not completely refractory to the tumor rechallenge.

FIG. 10. Adoptive immunity using splenocytes as immune cells. Spleen cells from mice successfully treated by Laser+SWNT-GC or Laser+SWNT were collected as immune cells. Spleen cells from untreated tumor-bearing mice were also used as control immune cells. Viable tumor cells were admixed with spleen cells from different mice, then injected into naive mice. The spleen cell to tumor cell ratio was 50,000,000:100,000 per mouse. The spleen cells from mice treated by Laser+SWNT-GC completely inhibited the tumor growth; all the mice in this group survived and none developed tumors. The spleen cells from Laser+SWNT-cured mice and control mice only provided 30% and 10% protections to the recipients, respectively.

DETAILED DESCRIPTION OF THE PREFERRED EMBODIMENTS

Materials and Methods

Figure 1A:
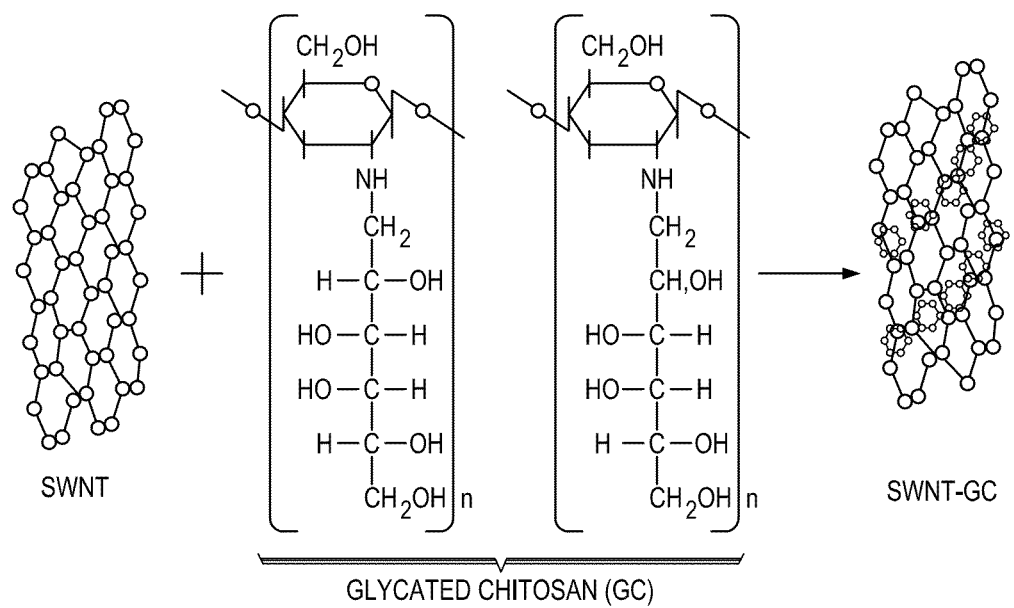
FIG. 1A. Schematic of the immunologically modified nanotube system, SWNT-GC.

CoMoCAT Single-Walled Carbon Nanotubes (SWNTs).

The CoMoCAT SWNT is used due to its unique properties of uniform size and NIR light absorption. The CoMoCAT method produces single-walled carbon nanotubes using a silica supported bimetallic cobalt-molybdate catalyst. The product is composed of a narrow distribution of nanotube types, with an average diameter of 0.81 nm. This type of nanotube has been of interest due to its absorption characteristics in the near-infrared region, especially as it possesses an intense absorption band at approximately 980 nm. Nanotubes of this type are discussed in "Carbon nanotube-enhanced thermal destruction of cancer cells in a noninvasive radiofrequency field" by Gannon C J, Cherukuri P, Yakobson B L, Cognet L, Kanzius J S, Kittrell C, Weisman R B, Pasquali M, Schmidt H K, Smalley R E, Curley S A (2007) in *Cancer* 110:2654-2665, "Multiphoton microscopy in life sciences" by König K (2000) in *J. Microsc.* (Oxford) 200:83-104, "Controlled production of single-wall carbon nanotubes by catalytic decomposition of CO on bimetallic Co—Mo catalysts" by Kitiyanan B, Alvarez W E, Harwell J H, Resasco D E (2000) in *Chem. Phys. Lett.* 317:497-503, and "Narrow (n,m)-distribution of single-walled carbon nanotubes grown using a solid supported catalyst" by Bachilo S M, Balzano L, Herrera J E, Pompeo F, Resasco D E, Weisman R B (2003) in *J. Am. Chem. Soc.* 125:11186-11187, each of which is hereby incorporated by reference.

Glycated Chitosan (GC).

GC is used as a special immunoadjuvant and as an effective surfactant for SWNT in this invention. GC was developed as an immunological stimulant for laser immunotherapy to treat metastatic tumors. GC is nontoxic in cell culture and in animal studies, as shown by previous experiments. GC may be synthesized by incubating an aqueous suspension of chitosan with a three-fold excess of galactose and subsequent stabilization by borohydride reduction of the mixture of Schiff bases and Amadori products as discussed in "Laser Immunotherapy: A Novel Treatment Modality for Metastatic Tumors" by Chen W R, Carubelli R, Liu H, Nordquist R E (2003) in *Mol. Biotechnol.* 25:37-43, hereby incorporated by reference. Examples of chitosan-derived biomaterials may be found in U.S. Pat. No. 5,747,475, the contents of which are hereby incorporated by reference. In addition to its immunodajuvant properties, the molecular structure of GC makes it a superb surfactant for SWNTs.

Preparation for SWNT-GC and SWNT-PEG Solutions.

CoMoCAT SWNT is used as an example of carbon nanotubes in this invention. Other nanostructures, such as nanoparticles, nanoclusters, and nanorods, can be used with GC to construct immunologically modified nanostructures. To prepare the SWNT-GC solution, pristine CoMoCAT SWNTs of 2.5-2.7 mg were mixed with 7-ml aqueous GC of different concentrations. It is contemplated that an amount within any subset of ranges within the range of 1-5 mg will also be effective. To disperse the SWNTs, the mixture was sonicated for 30 minutes using an ultrasonic processor. This suspension of SWNTs was then centrifuged at 30,150 g for 30 minutes. The final concentration of SWNT in GC solution was determined by comparing its optical absorbance with that of a calibration SWNT solution of known concentration.

Optical Spectra Measurements.

The optical absorbance of SWNT-GC was measured by a UV-vis absorption spectrophotometer. To take advantage of the intrinsic optical properties of SWNTs, Raman spectroscopy was used to verify the SWNT-GC conjugation using capillaries without spinning or stirring during the measurements. An argon ion laser (514.5 nm) was used for excitation in combination with a 40× objective of a microscope, a spectrometer, and a CCD detector. After focusing on the center of the capillary, the Raman spectrum of the sample was recorded with a resolution of 2 $cm^{-1}$ (10 mW power, 20 seconds collection time).

Selective Photothermal Effects of Laser+SWNT-GC Using Gel Phantoms.

SWNT with a 978 nm absorption peak was used for the SWNT-GC suspension. Gel phantom was mixed with SWNT-GC suspension to simulate absorption-enhanced targets. A 980-nm laser was used to irradiate both SWNT-GC gel samples and normal gel samples. Temperature increases at a depth of 4 mm below the gel surface was measured by thermocouples. The surface temperatures of gel phantoms with and without SWNT-GC enhancement during laser irradiation were measured using an infrared thermal camera.

Using a magnetic resonance imager, the temperature distribution inside a gel phantom during laser irradiation was measured. The gelatin gel was placed in a cylinder container. The temperature distributions inside a normal gel block, before and during laser irradiation were also measured. To enhance the gel absorption, a gel sphere of 0.5-cm radius containing SWNT-GC suspension was imbedded in the gel 1 mm beneath the surface to simulate a deep target tumor. The temperature distribution inside the SWNT-GC enhanced gel block, before and during laser irradiation, were measured.

Cell Culture.

Murine mammary tumor line EMT6 cells and murine macrophage line RAW264.7 cells were used in the experiments. The cells were cultured in RPMI 1640 (GIBCO) supplemented with 15% fetal calf serum (FCS), penicillin (100 units/ml), and streptomycin (100 µg/ml) in 5% $CO_2$, 95% air at 37° C. in an humidified incubator.

GC-FITC and SWNT-GC-FITC Functionalization.

FITC (13 mM, 50 µl) was dissolved in DMSO, and then mixed with 1 ml GC or SWNT-GC solutions. After incubating the mixture for overnight at room temperature, avoiding light exposure, the GC-FITC or SWNT-GC-FITC solutions were filtrated through 100 KDa filters (Millipore) to remove excess FITC. Then GC-FITC and SWNT-GC-FITC were incubated with EMT6 tumor cells for 2 hours and the fluorescence of FITC from the cells was detected using laser scanning microscope.

Cell Viability Assays.

Tumor cells (1×104 per well) in 24-well tissue culture plates were incubated with different combinations of SWNT and GC for 2 hours, rinsed with PBS, and exposed to light at a fluence of 60-150 $J/cm^2$ (0.5-1.25 $W/cm^2$ for 2 min). The light source was a 980-nm semiconductor laser.

Cell cytotoxicity in vitro was performed with a colorimetric tetrazolium salt-based assay, Cell Counting Kit-8 (CCK8). To detect photothermal cytotoxicity, tumor cells were irradiated by a 980-nm laser with or without incubation with SWNT-GC, OD450, the absorbance value at 450 nm, was read with a 96-well plate reader, to determine the viability of the cells.

Detection of TNFα.

To detect TNFα secretion by macrophages when stimulated by tumor cells after treatments, macrophages were incubated with treated tumor cells in 24-well tissue culture plates. After 24 hours of incubation, the supernatants were collected for ELISA detection.

Animal Tumor Model.

EMT6 cells (1×10$^6$) in a 0.1-ml solution were injected into the flank region of female Balb/c mice, aged 6-8 weeks. Animals were used in experiments 7 to 10 days after tumor cell inoculation, when the tumors reached a size of approximately 300 $mm^3$.

Treatment of Animal Tumors Using Laser+SWNT-GC.

Tumor-bearing mice were divided into different treatment groups (12-16 mice/group). A solution of 0.1-ml containing 5 mg/ml (25 mg/kg) GC or 0.2 mg/ml (1 mg/kg) SWNT or 0.2 mg-5 mg/ml (1 mg-25 mg/kg) SWNT-GC was directly injected into the center of each tumor, 2 hours before irradiation with a 980-nm laser. The light was delivered to the tumor using a fiber optic delivery system. The power density at the treatment area, which encompassed the tumor and 0.5 to 1 cm of the surrounding skin, was 0.75 W/cm$^2$ for a treatment duration of 10 minutes. During laser irradiation, mice were anesthetized with an intraperitoneal injection of pentobarbital sodium and were restrained in a specially designed holder. After treatment, the mice were observed daily and the tumors were measured every other day for a period of 100 days.

Adoptive Immunity Transfer.

Mice successfully treated by Laser+SWNT-GC and Laser+SWNT were challenged with an increased tumor dose of 2×10$^6$ cells per mouse. At the same time, control mice of the same age were inoculated with the same number of tumor cells. Twenty-eight days after the tumor inoculation, the mice were terminated by cervical dislocation, and their spleens were dissected free of fat. Spleen cell suspensions were prepared by mechanical disruption into medium with 10% FCS. Spleen cells and viable tumor cells were counted on a hemocytometer before admixed. The admixture had a 500:1 spleen to tumor cell ratio. Naive mice were inoculated with a 0.2-ml admixture containing 5×10$^7$ spleen cells and 10$^5$ tumor cells.

Seven days after treatment with different combinations of laser, SWNT, and GC, splenocytes from treated mice were cultured in the presence of EMT6 tumor cells for 5 days, after which cell cytotoxicity was assessed with CCK8.

Results

Characterization of SWNT-GC.

Figure 1B:
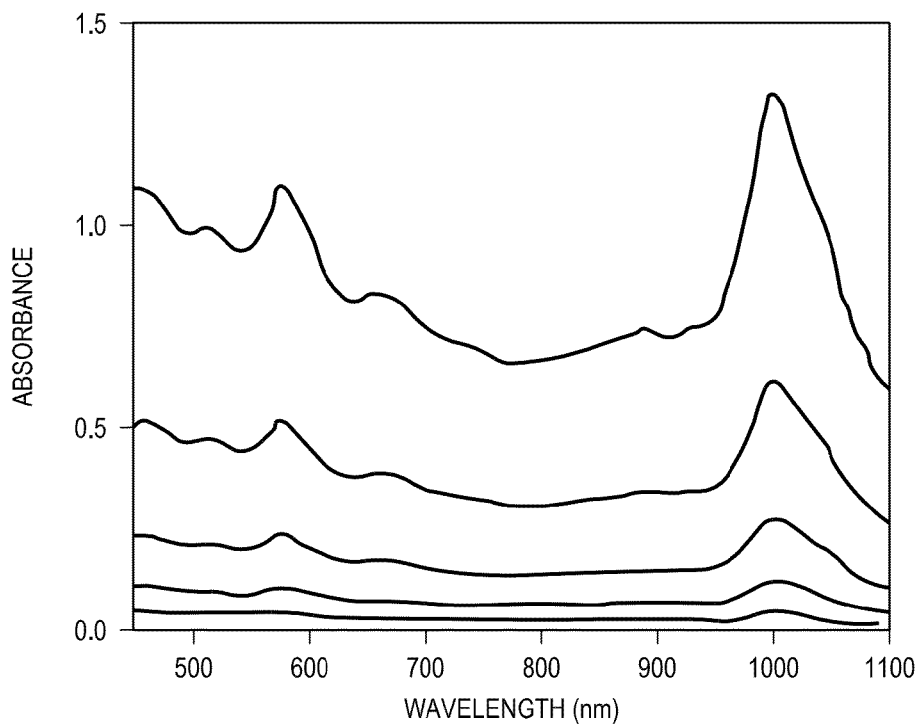
FIG. 1B. Absorption spectra of SWNT-GC suspension with different SWNT-GC concentrations (top curve, SWNT-GC concentration: 135 µg/ml-0.73 wt %; lower curves correspond to consecutive 50% reduction in SWNT-GC concentration).
Figure 1C:
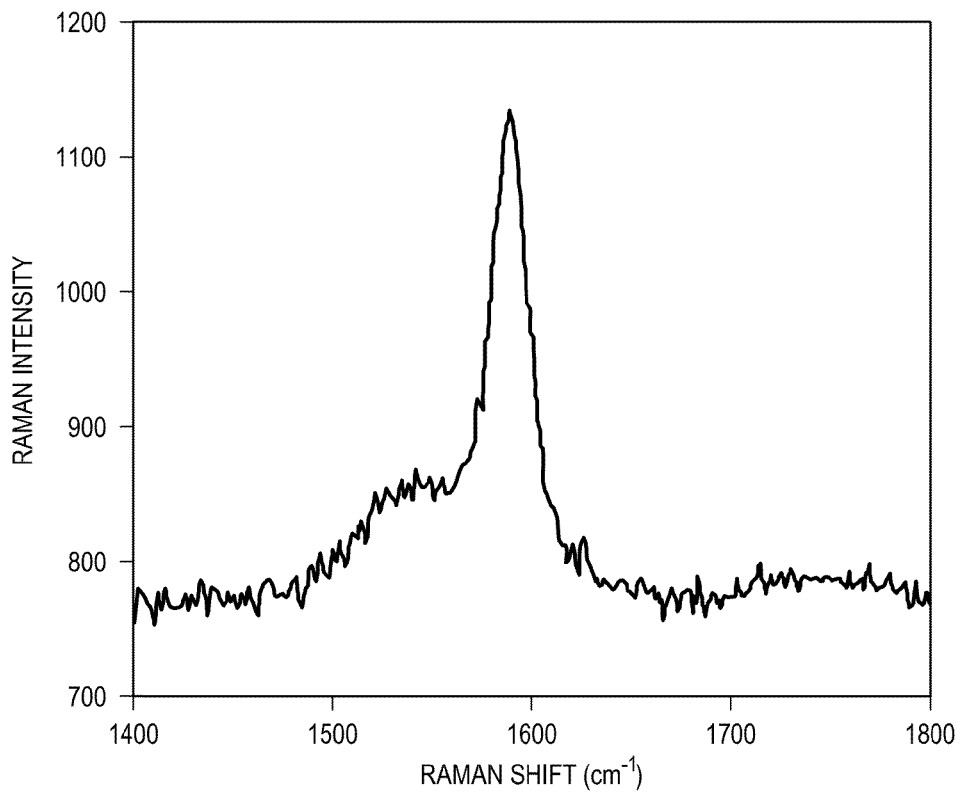
FIG. 1C. Raman spectra of SWNT-GC.

A stable SWNT-GC suspension was obtained after the final centrifugation of the solution. The schematic of SWNT-GC is given in FIG. 1A. The near infrared absorption spectra of SWNT-GC exhibit a strong band around 980 nm (FIG. 1B), which is typical for CoMoCAT samples. The Roman spectra of SWNT-GC is given in FIG. 1C. The optical absorbance of the GC solution in this spectral window is extremely low.

The resonance ratio for the SWNT suspension in GC was measured to be 0.140, which favorably compares to NaCholate (with a similar ratio of 0.147), one of the best surfactants reported in literature. The SWNT-GC suspension remained stable after storage for more than six months at 4° C.

Figure 2A:
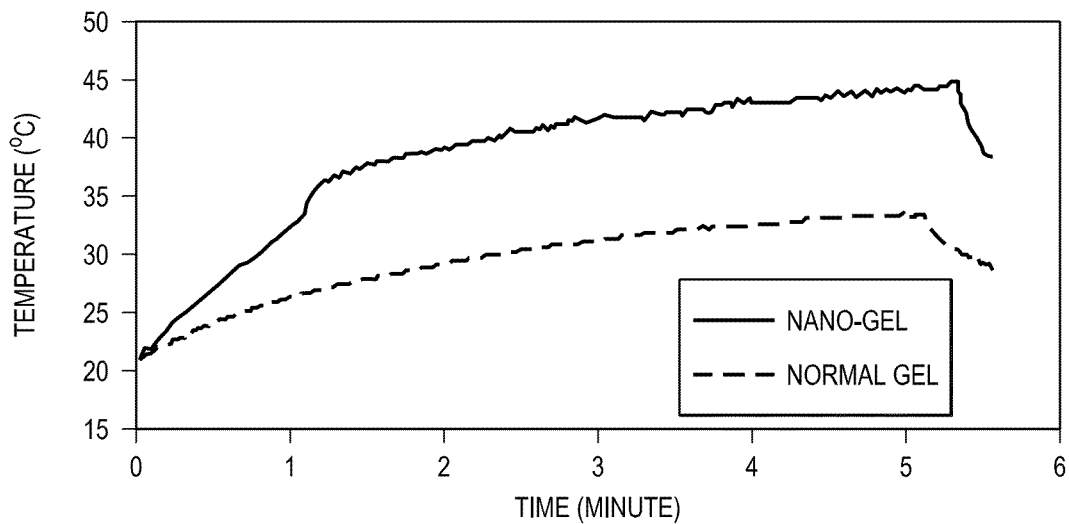
FIG. 2A. Selective photothermal effects using SWNT-GC and laser irradiation (thermocouple measurement). Temperature inside gel phantoms (with or without nanotube enhancement) was measured by thermocouples during irradiation by a 980-nm laser. The laser power density was 1.13 W/cm² and irradiation duration was 5 minutes. The thermocouples were placed 4 mm below the sample surfaces.
Figure 2B:
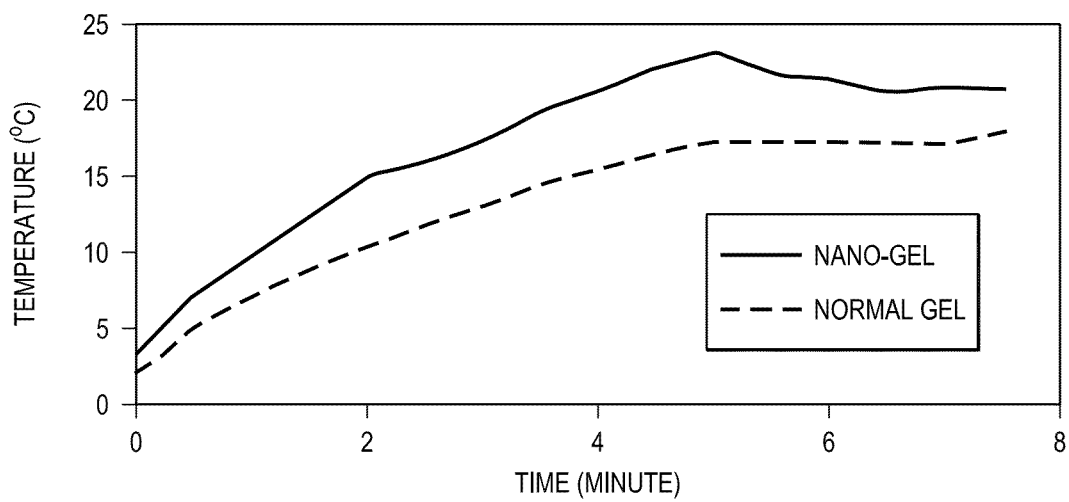
FIG. 2B. Selective photothermal effects using SWNT-GC and laser irradiation (infrared thermal camera measurement). Temperature increase on the surface of gel phantoms (with or without nanotube enhancement) was measured during laser irradiations by an infrared thermal camera. The laser power density was 1.13 W/cm$^2$ and irradiation duration was 5 minutes.

Using SWNT-GC for light absorption enhancement, temperature increases at a depth of 4 mm below the surface of the gel phantom was measured by thermocouples. As shown in FIG. 2A, a 12° C. differential temperature increase was obtained between SWNT-GC enhanced gel and normal gel. The surface temperature increases of refrigerated samples are shown in FIG. 2B. Under the same conditions, these increases demonstrate the selectivity of SWNT-GC at 980 nm. The temperature increase of the target sample can be controlled by adjustment of the SWNT-GC concentration and laser settings.

Figure 3A:
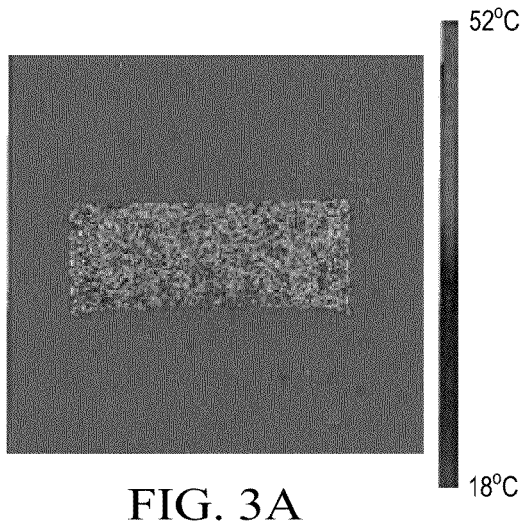
FIG. 3A. Temperature distribution in a gel phantom without nanotube enhancement before laser irradiation (magnetic resonance thermometry measurement).
Figure 3B:
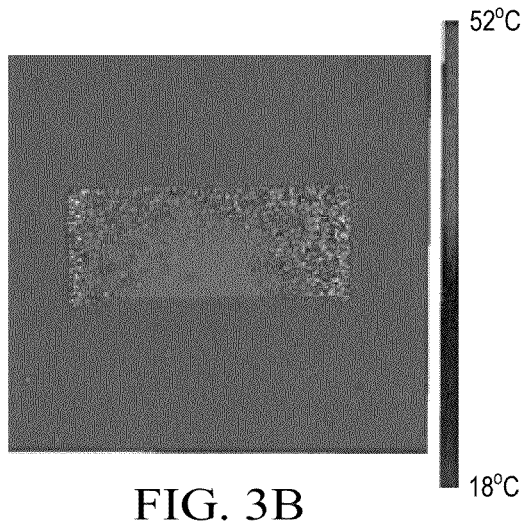
FIG. 3B. Temperature distribution in a gel phantom without nanotube enhancement after laser irradiation (magnetic resonance thermometry measurement). The sample was irradiated by a 980-nm laser from the bottom. The power density was 0.212 W/cm$^2$ with a beam diameter of 3.0 cm. This figure shows the temperature distribution 7 minutes after laser radiation.
Figure 3C:
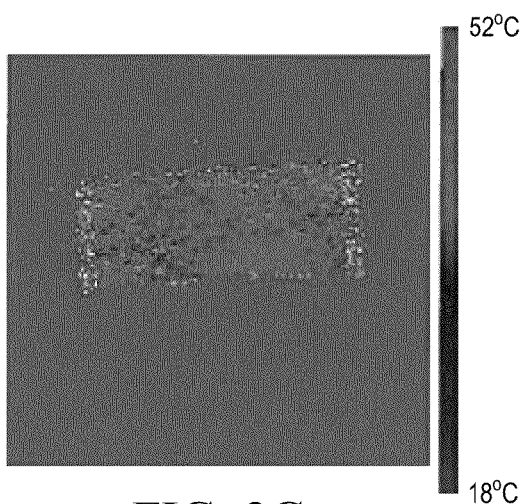
FIG. 3C. Temperature distribution in a gel phantom with nanotube enhancement before laser irradiation (magnetic resonance thermometry measurement). A nanotube enhanced spherical gel was buried 1 mm below the surface.
Figure 3D:
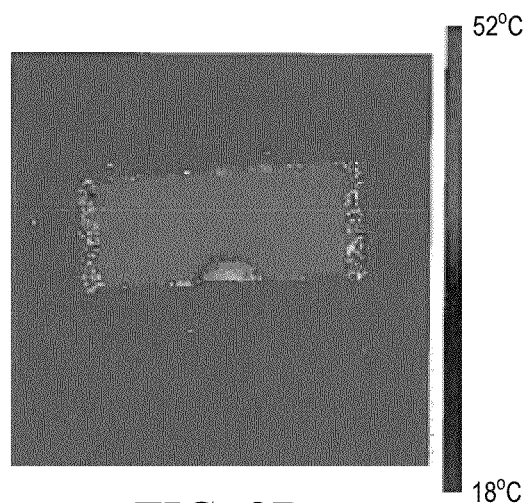
FIG. 3D. Temperature distribution in a gel phantom with nanotube enhancement after laser irradiation (magnetic resonance thermometry measurement). A nanotube enhanced spherical gel was buried 1 mm below the surface. The sample was irradiated by a 980-nm laser from the bottom. The power density was 0.212 W/cm$^2$ with a beam diameter of 3.0 cm. This figure shows the temperature distribution 7 minutes after laser radiation.

The temperature distributions inside a normal gel block, before and during laser irradiation, obtained by magnetic resonance thermometry, are shown in FIGS. 3A and 3B. The temperature distribution inside the SWNT-GC enhanced gel block, before and during laser irradiation, are shown in FIGS. 3C and 3D. The results show a higher temperature increase in the SWNT-GC enhanced target.

Figure 4:
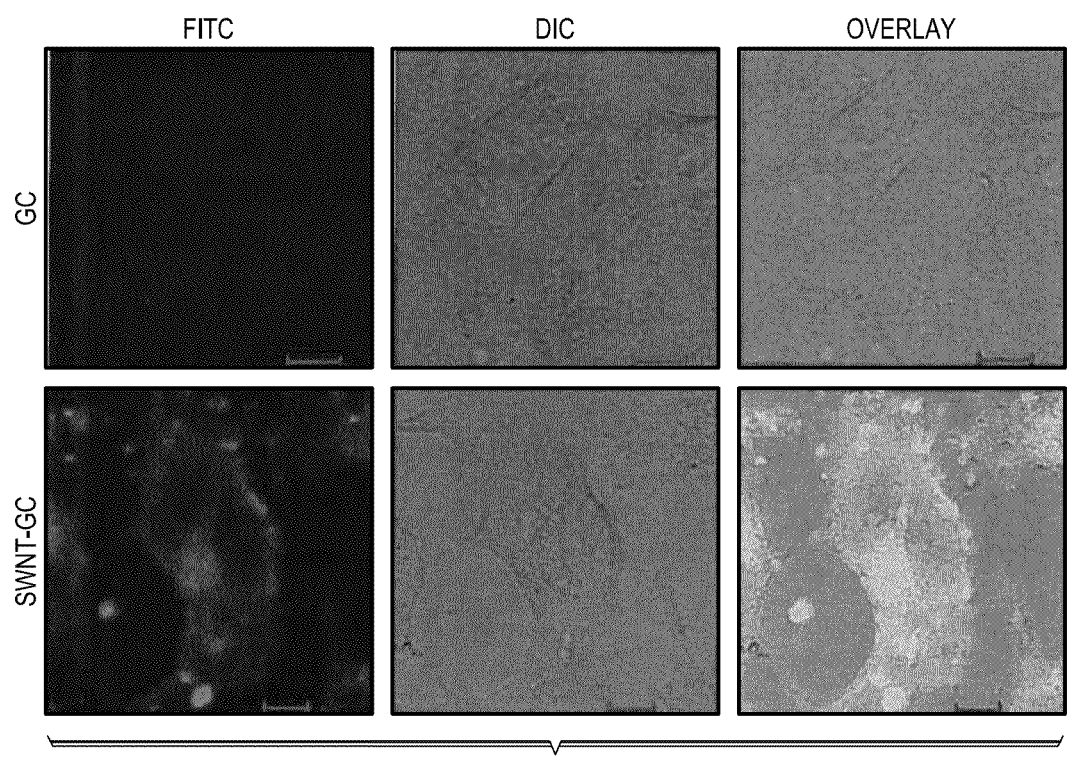
FIG. 4. Subcellular distribution of GC carried by SWNT and transported into the tumor cells. The fluorescence images of SWNT-GC-FITC (SWNT-GC conjugated to a fluorescent dye FITC) and GC-FITC (GC conjugated to a fluorescent dye FITC) in EMT6 cells were acquired. Cells were incubated with SWNT-GC-FITC and GC-FITC for 2 hours, and the fluorescence of FITC from cells was detected by laser scanning microscope. Note that GC could enter cells only when attached to SWNT. Bar=10 μm.

To confirm that SWNT could carry GC into tumor cells, SWNT-GC was functionalized with FITC, a fluorescent tag, and the fluorescence emission from the tumor cell incubated with SWNT-GC-FITC or GC-FITC was observed. Confocal images of the EMT6 cells show that SWNT-GC-FITC accumulates mainly in the cytoplasm, while GC-FITC is absent inside the cells (FIG. 4).

These results indicate that, as a unique quasi one-dimensional material, SWNT can carry GC into tumor cells, which fulfilled a crucial step for temporally and spatially synchronized photothermal and immunological reactions in the target tumor cells under laser irradiation.

To determine the cytotoxicity of SWNT-GC under laser irradiation, EMT6 tumor cells were incubated with the SWNT-GC solution for 2 hours, followed by irradiation with a 980-nm laser. Tumor cytotoxicity depended on both the SWNT-GC concentration and the laser dose (FIG. 5).

In Vitro Immune Stimulation of SWNT-GC.

Figure 6A:
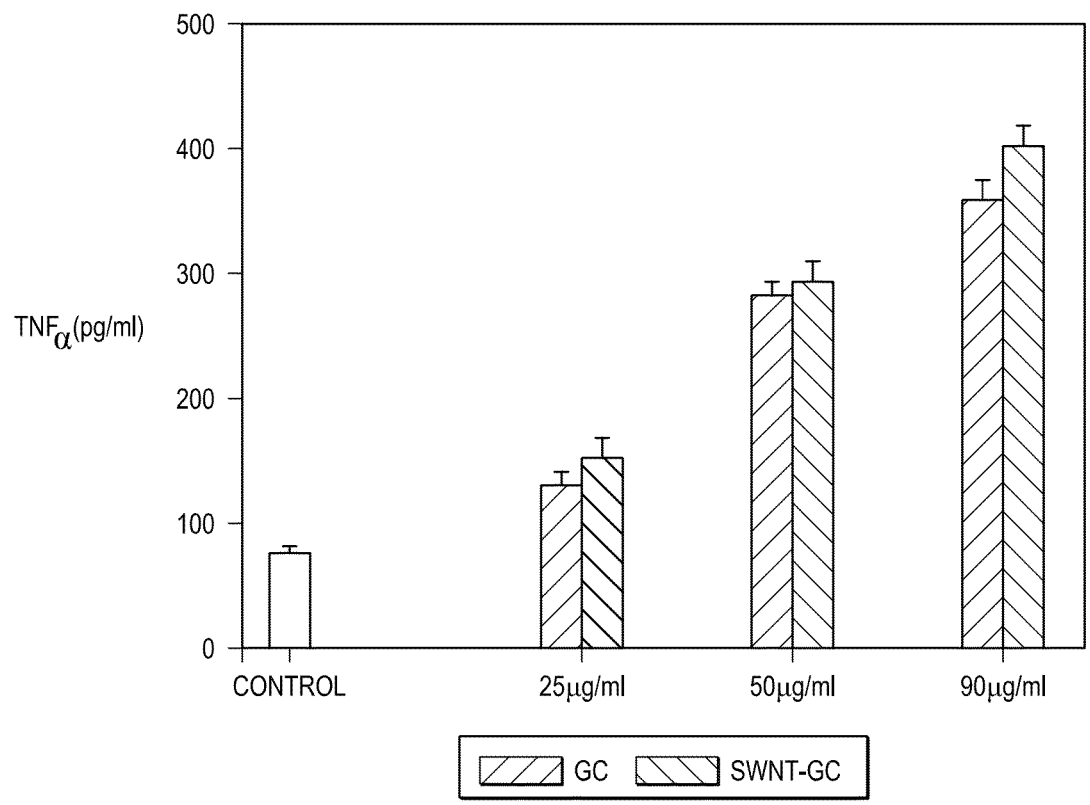
FIG. 6A. In vitro immunological effects of SWNT-GC. TNFα secretion by murine macrophages incubated with GC or SWNT-GC suspensions, detected by ELISA. Macrophages were incubated with GC solution of different concentrations (25, 50, and 90 μg/ml, gray bars) or with SWNT-GC solution of different concentrations (2.5 μg-25 μg, 2.5 μg-50 μg, and 2.5 μg-90 ng/ml, black bars) for 24 hours. After incubation, supernatants were collected for the determination of TNFα. Bars, means±SD (n=4).

Immunological observations showed that GC and SWNT-GC stimulated a similar level of TNFα secretion at a given concentration, when incubated with murine macrophages, and the level of TNFα secretion increased with GC concentration (FIG. 6A). These results showed that the stable SWNT-GC suspension retained the immunological capability of GC.

To determine the immunological responses induced by treated tumor cells, ELISA was performed to measure TNFα secreted by macrophages incubated with tumor cells after different treatments for 24 hours. As shown in FIG. 6B, tumor cells incubated with either GC or SWNT-GC could stimulate a certain level of TNFα secretion, whereas a low dose laser irradiation (60 J/cm$^2$) alone did not enhance the activation of macrophages. Tumor cells treated by higher doses of laser irradiation (120 or 150 J/cm$^2$) also stimulated TNFα secretion by macrophages, due to laser induced cell death. However, at these high light doses, tumor cells treated by Laser+SWNT-GC resulted in much higher levels of TNFα secretion (FIG. 6B).

In Vivo Effects of SWNT-GC.

EMT6 cells were injected subcutaneously in the flank of Balb/c female mice. After the tumor size reached approximately 300 mm$^3$, the animals were divided into eight different treatment groups. After treatment, the mice were observed daily and the tumor volume was measured using a caliper every other day. The mice treated by injections of SWNT (1 mg/kg, in PEG), GC (25 mg/kg), or SWNT-GC (1 mg-25 mg/kg) had an average tumor burden similar to that of untreated control mice (FIG. 7A); none of the mice in these three groups exhibited tumor regression. In contrast, mice treated by laser irradiation (0.75 W/cm$^2$ for 10 min) had an average tumor burden noticeably smaller than that of the control mice (FIG. 7B). Laser+SWNT and Laser+SWNT-GC treatments resulted in significant tumor suppression (FIG. 7B).

For survival studies, sixteen mice were used per each treatment group and the mice were monitored for 100 days after tumor inoculation. Among mice treated by a single injection of SWNT, GC, or SWNT-GC solution, there were no long-term survivors, although mice in GC and SWNT-GC groups had a slightly longer average survival time (FIG. 8A). Under laser irradiation at a power density of 0.75 W/cm$^2$, the survival rates were 100% in the Laser+SWNT-GC group, 56% in the Laser+SWNT group, 38% in the Laser+GC group, and 25% in the Laser only group, respectively (FIG. 8B). Nine of the sixteen mice in the Laser+SWNT group survived, but complete tumor regression was observed in only three mice, while no complete tumor regression was observed in the Laser+GC or the Laser only groups. Overall, the results in FIG. 8 demonstrate that the Laser+SWNT-GC combination is the most efficacious treatment, resulting in a much higher survival rate and stronger tumor suppression than other combinations of laser, SWNT, and GC.

Rechallenge of the Cured Mice.

Mice successfully treated by Laser+SWNT-GC and Laser+SWNT were challenged with $2 \times 10^6$ viable tumor cells 100 days after the initial tumor inoculation (10 mice per group). Ten naive mice of the same age were inoculated with $2 \times 10^6$ viable tumor cells per mouse as controls. As shown in FIG. 9, all the Laser+SWNT-GC cured mice showed total resistance to the challenge. However, all the Laser+SWNT cured mice developed primary tumors and died within 80 days of tumor re-challenge. All the control mice developed primary tumors and died within 40 days of tumor inoculation. The Laser+SWNT-GC cured mice were challenged a second time with an increased tumor dose ($3 \times 10^6$/mouse). Again, they were completely refractory to the tumor rechallenge.

Adoptive Immunity Transfer.

Spleen cells from mice successfully treated by Laser+SWNT-GC or Laser+SWNT were harvested as immune cells. As controls, spleen cells from untreated tumor-bearing mice were also collected. The spleen cells were admixed with viable tumor cells at a ratio of 500:1. Naive mice were inoculated by $10^5$ viable tumor cells with $5 \times 10^7$ spleen cells harvested from mice of different treatment groups. FIG. 10 shows the survival rates of mice inoculated with the mixture of spleen cells and tumor cells. The spleen cells from Laser+SWNT-GC cured mice provided 100% protection to the recipients, while the spleen cells from Laser+SWNT cured mice protected only 30% of the recipients. The spleen cells from control tumor-bearing mice provided only 10% protection to the recipients (FIG. 10). Sixty days after adoptive immunity transfer, all the mice protected by the spleen cells from Laser+SWNT-GC-cured mice were challenged again with $2 \times 10^6$ tumor cells; all mice withstood the second challenge.

Discussion

The ideal treatment modality for cancer, particularly metastatic cancer, should achieve a systemic, tumor-specific immunological response through a minimally invasive, local intervention. Such an approach could potentially suppress local tumors and at the same time eradicate metastases at distant sites, while providing anti-tumor immunity to the host with minimal adverse side effects. Photothermal reaction using lasers is an ideal local intervention due to its precise energy delivery to target tissue and the sensitivity of tumor tissue to temperature increase.

Laser light in the NIR region, in combination with appropriate light-absorbing agents, is particularly attractive for selective photothermal interaction, because of the low absorbance of biological tissue in the NIR region.

SWNTs have been used as therapeutic targets to induce thermal injury to cancer cells. It has been shown that death of cancer cells with internalized SWNTs could be induced by exposure to either continuous NIR light or radiofrequency radiation.

Anti-tumor immune response can be significantly enhanced by introducing immunological stimulants to the tumors, particularly when combined with other interventions. When used appropriately, such immunostimulants can significantly improve the efficacy of cancer treatment by stimulating the host immune system, such as when *Corynebacterium parvum*, bacille Calmette-Gue'rin, or other immunoadjuvants were intratumorally administered in conjunction with phototherapy treatment.

SWNTs by CoMoCAT method are uniform in size and have a strong absorption peak around 980 nm, hence an ideal light-absorbing agent for the desired selective photothermal interaction in local intervention. The selective photothermal laser-tissue interaction using the 980-nm laser and CoMoCAT SWNT has been demonstrated through in vitro and in vivo experiments.

GC has also been used previously as an immunoadjuvant for cancer treatment in animal studies. The purpose of the proposed novel SWNT-GC system is to further improve the laser immunotherapy. The molecular structures of CoMoCAT SWNTs and GC allow a stable, uniform SWNT suspension using GC as an effective surfactant (FIG. 1). The experimental results clearly show that the SWNT-GC solution retained the optical properties of SWNT (FIGS. 2 and 3) and the immunological properties of GC.

The combination of SWNT-GC due to the electrical structure of both SWNT and GC also provides this novel system a unique advantage: carrying GC into the tumor cells. Usually, immunological stimulants like glycated chitosan, a long-chain polymer, cannot enter cells directly, as evidenced by the experimental results (FIG. 4, top panel). SWNT has shown a capability to enter cells and localize in different subcellular components depending on the molecules SWNT is carrying. When GC is conjugated with SWNT, it can be carried into tumor cells (FIG. 4, bottom panel). GC inside tumor cells can serve as exogenous immunological stimulant, hence further enhancing the immune responses induced by the combined photothermal and immunological reactions by laser+SWNT-GC.

The advantage of the SWNT-GC system lies in its simultaneous, synergistic photothermal and immunological reactions during tumor treatment. Specifically, SWNT selectively absorbs the 980-nm laser light to induce tumor cell destruction, hence providing an exogenous cellular stress and tumor immunogen to the host. In addition, GC enhances the immune response at the same photothermal treatment site due to its conjugation with SWNT. Therefore, because of the unique bound of SWNT and GC, they can target the same tumor cell at the same time, resulting in synergistic photothermal and immunological reactions.

The in vitro and in vivo results demonstrated the effectiveness of Laser+SWNT-GC in the treatment of animal tumors.

While GC or SWNT-GC alone did not cause tumor cell death in vitro, combining with laser irradiation, particularly at higher doses (120 and 150 $J/cm^2$), they could significantly increase cytotoxicity (FIG. 5). Similarly, Laser+SWNT-GC treated tumor cells could induce much higher levels of TNFα secretion from macrophages, as shown by the data in FIG. 6. These results demonstrate the synergistic effect of laser irradiation, light absorption of SWNT, and immunological stimulation of GC.

The synergy between laser, SWNT, and GC was further demonstrated by in vivo experimental results, as shown in FIG. 7. Intratumoral injections of SWNT, GC, or SWNT-GC did not result in tumor regression (FIG. 7A), although treatments using single components with GC (GC or SWNT-GC) prolonged the medium survival time of the mice (FIG. 8A). These results could be attributed to the nonspecific immune response of host, induced by GC, to enhance the tumor resistance, although such a response could not selectively destroy tumor cells, as evidenced by both in vitro (FIG. 5) and in vivo (FIG. 7A) results. When laser irradiation was used, the effect of SWNT-GC was significantly enhanced, both in vitro (FIG. 5) and in vivo (FIG. 7B). The treatment of Laser+SWNT-GC resulted in complete tumor suppression, while the treatment of Laser+SWNT also resulted in significant tumor suppression (FIG. 7B). Specifically, with a laser power density 0.75 $W/cm^2$ and irradiation duration of 10 minutes, the Laser+

SWNT-GC achieved a 100% cure rate, much higher than the cure rate of 56% with the Laser+SWNT treatment (FIG. 8B).

Mice successfully treated by Laser+SWNT-GC withstood subsequent challenges with increased tumor dose; all the cured mice in this group showed total resistance to the tumor rechallenge (FIG. 9). However, the mice successfully treated with the Laser+SWNT all developed primary tumors and died about 80 days after the tumor rechallenge (FIG. 9). These results demonstrate the essential role of GC in inducing long-lasting anti-tumor immunity.

Splenocytes from mice cured by Laser+SWNT-GC provided 100% protection to normal recipient mice when the animals were injected with a mixture of the spleen cells and tumor cells, as shown in FIG. 10. In comparison, splenocytes from mice cured by Laser+SWNT only provided partial protection to the recipient mice (FIG. 10). These results indicate that Laser+SWNT-GC induced a long-term memory in immune cells, again, attributed to the effect of GC.

It is hypothesized that the mechanism of Laser+SWNT-GC in the treatment of tumors lies in the synergistic reactions between the selective photothermal reaction and immunological stimulation. The photothermal reaction reduces the tumor burden and at the same time exposes the tumor antigens; the immunoadjuvant in situ first stimulates the host immune system and then directs the immune system against the specific tumor cells. In each individual host, in fact, laser immunotherapy produced an in situ auto vaccine. This tandem effect not only resulted in total tumor eradication but also led to a long-term tumor-specific immunity. This method, therefore, provides a systemic immunotherapy through local intervention for each individual host without the usually required immune cross-reactivity.

In the present disclosure, an immunoadjuvant has been used as a surfactant to effectively disperse nanotubes to provide synergistic photothermal and immunological effects under laser irradiation. This system of the disclosure, due to its unique optical properties and immunological functions, could be used in the treatment of tumors, particularly metastatic tumors. The system of the invention, due to the strong binding of SWNT and GC, allowed GC being carried into the tumor cells, further enhancing the photothermal and immunological effects of laser+SWNT-GC.

In summary, selective photothermal interaction and tumor-specific immunological stimulation provided by Laser+SWNT-GC, which simultaneously target the tumor cells spatially and temporally, are contemplated for use as an effective cancer treatment therapy.

* * * *

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art.

The invention claimed is:

1. A method of delivering an immunostimulant to a cell body and of producing targeted, synergistic photophysical and immunological reactions comprising:
   coating a nanostructure with glycated chitosan;
   penetrating a cell membrane of a cell body with said nanostructure;
   irradiating said nanostructure after said step of penetrating; wherein
   said nanostructure is a singled-walled carbon nanotube; and wherein
   said step of irradiating comprises exposing said cell body with near-infrared light for facilitating synergistic, simultaneous photothermal and immunological reactions.

2. The method according to claim 1 wherein:
said near-infrared light is produced by a 980-nm laser.

3. The method according to claim 2 wherein:
said laser has a laser power density of 0.75 to 2 W/cm; and
said step of irradiating comprises administering said laser with an irradiating duration of 10 to 30 minutes.

4. The method according to claim 1 wherein:
said step of irradiating comprises exposing said cell body with radiofrequency radiation for facilitating synergistic, simultaneous photothermal and immunological reactions.

5. The method according to claim 1 further comprising the step of:
   dissolving and stabilizing said nanostructure with an immunostimulant.

6. The method according to claim 1 wherein:
said nanostructure has an absorption peak in the range of 800 to 1200 nm.

* * * * *

UNITED STATES PATENT AND TRADEMARK OFFICE
CERTIFICATE OF CORRECTION

| | | |
|---|---|---|
| PATENT NO. | : 9,107,944 B2 | Page 1 of 1 |
| APPLICATION NO. | : 13/755105 | |
| DATED | : August 18, 2015 | |
| INVENTOR(S) | : Chen | |

It is certified that error appears in the above-identified patent and that said Letters Patent is hereby corrected as shown below:

In the specification, Column 1, line 12, insert the following statement:

--STATEMENT AS TO RIGHTS TO INVENTIONS MADE UNDER FEDERALLY SPONSORED RESEARCH OR DEVELOPMENT
    This invention was sponsored in part by OK-INBRE (Oklahoma IDeA Network of Biomedical Research Excellence). The OK-INBRE is a grant from the National Center for Research Resources of the National Institutes of Health through Grant Number P20RR016478.--

In the claims, Claim 3, Column 12, line 30, please make the following change:

Replace "2 W/cm" with -- $2\ W/cm^2$ --

Signed and Sealed this
Fifteenth Day of March, 2016

Michelle K. Lee
*Director of the United States Patent and Trademark Office*